United States Patent
Yoshida et al.

(10) Patent No.: US 11,229,593 B2
(45) Date of Patent: Jan. 25, 2022

(54) HAIR COSMETIC

(71) Applicant: KAO CORPORATION, Tokyo (JP)

(72) Inventors: Hiroshi Yoshida, Utsunomiya (JP);
Yuta Sakai, Yoshikawa (JP); Masutaro Hirayama, Wakayama (JP); Shingo Komaba, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/765,033

(22) PCT Filed: Nov. 19, 2018

(86) PCT No.: PCT/JP2018/042675
§ 371 (c)(1),
(2) Date: May 18, 2020

(87) PCT Pub. No.: WO2019/098365
PCT Pub. Date: May 23, 2019

(65) Prior Publication Data
US 2020/0397680 A1    Dec. 24, 2020

(30) Foreign Application Priority Data
Nov. 20, 2017 (JP) .............................. JP2017-223220

(51) Int. Cl.
| | | |
|---|---|---|
| *A61Q 5/10* | (2006.01) | |
| *A61K 8/49* | (2006.01) | |
| *A61K 8/24* | (2006.01) | |
| *A61K 8/365* | (2006.01) | |
| *A61K 8/41* | (2006.01) | |
| *A61K 8/46* | (2006.01) | |
| *A61K 8/81* | (2006.01) | |
| *A61Q 5/02* | (2006.01) | |

(52) U.S. Cl.
CPC .............. *A61K 8/492* (2013.01); *A61K 8/24* (2013.01); *A61K 8/365* (2013.01); *A61K 8/416* (2013.01); *A61K 8/463* (2013.01); *A61K 8/8129* (2013.01); *A61K 8/8158* (2013.01); *A61K 8/8182* (2013.01); *A61Q 5/02* (2013.01); *A61Q 5/10* (2013.01); *A61K 2800/5426* (2013.01); *A61K 2800/596* (2013.01)

(58) Field of Classification Search
CPC . A61Q 5/10; A61Q 5/02; A61K 8/416; A61K 8/492; A61K 8/463; A61K 8/365; A61K 2800/5426; A61K 8/24; A61K 2800/596; A61K 8/8182
USPC .......................................................... 8/405
See application file for complete search history.

(56) References Cited

U.S. PATENT DOCUMENTS

| | | | | |
|---|---|---|---|---|
| 5,743,919 | A * | 4/1998 | Moeller ................. | A61K 8/492 8/405 |
| 2003/0051297 | A1* | 3/2003 | Patel ........................ | A61K 8/22 8/405 |
| 2010/0037404 | A1* | 2/2010 | Koike ..................... | A61K 8/891 8/423 |
| 2010/0125956 | A1 | 5/2010 | Koike et al. | |
| 2010/0154135 | A1 | 6/2010 | Matsunaga et al. | |

FOREIGN PATENT DOCUMENTS

| | | |
|---|---|---|
| EP | 1 254 650 A2 | 11/2002 |
| EP | 1 792 951 A2 | 6/2007 |
| GB | 2 191 780 A | 12/1987 |
| JP | 2003-55175 A | 2/2003 |
| JP | 2004-525130 A | 8/2004 |
| JP | 2007-326807 A | 12/2007 |
| JP | 2007-326810 A | 12/2007 |
| JP | 2009-137877 A | 6/2009 |

(Continued)

OTHER PUBLICATIONS

STIC Search Report dated Jun. 15, 2021.*
U.S. Appl. No. 16/765,061, filed May 18, 2020, Sakai, Yuta et al.
U.S. Appl. No. 16/765,033, filed May 18, 2020, Yoshida, Hiroshi et al.
U.S. Appl. No. 16/765,046, filed May 18, 2020, Nagayama, Ayami.
U.S. Appl. No. 16/765,038, filed May 18, 2020, Shimazu, Ayako et al.
U.S. Appl. No. 16/765,067, filed May 18, 2020, Shimazu, Ayako et al.

(Continued)

*Primary Examiner* — Eisa B Elhilo
(74) *Attorney, Agent, or Firm* — Oblon, McClelland, Maier & Neustadt, L.L.P.

(57) ABSTRACT

The present invention relates to a hair cosmetic containing the following components (A) to (E):
(A) a compound represented by the following general formula (1) or a salt thereof:

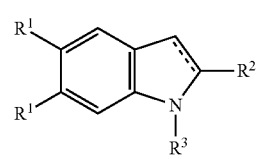

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;
(B) an alkaline agent;
(C) a buffering agent;
(D) an anionic surfactant; and
(E) a cationic polymer having a cation charge density of 0.01 meq/g or more and 4.8 meq/g or less,
a mass ratio of the component (A) to the component (E) [(A)/(E)] being 0.05 or more and less than 2.

15 Claims, No Drawings

(56) References Cited

FOREIGN PATENT DOCUMENTS

JP      2014-024766 A    2/2014
WO   WO 2008/149535 A1   12/2008

OTHER PUBLICATIONS

International Search Report dated Dec. 18, 2018 in PCT/JP2018/042675 filed on Nov. 19, 2018, 2 pages.
Extended European Search Report dated Jul. 29, 2021 in European Patent Application No. 18879046, 8 pages.

* cited by examiner

HAIR COSMETIC

FIELD OF THE INVENTION

The present invention relates to a hair cosmetic.

BACKGROUND OF THE INVENTION

Conventionally, as a hair dye for gray hair dyeing, an air-oxidative hair dye using 5,6-dihydroxyindole, 5,6-dihydroxyindoline, or a derivative thereof, each of which is a melanin precursor, is known. Such a melanin precursor does not use an oxidizing agent, and therefore, even in the case of being used for a hair dye, it is less in damage of the hair, and it is high in convenience as a dye for hair dye.

For example, PTL 1 discloses an aerosol type one-part hair dye composition containing the aforementioned melanin precursor, a predetermined sulfate type surfactant, a predetermined polyethoxylate, and a thickening polymer, which is excellent in foam stability and is easily applied on hair.

CITATION LIST

Patent Literature

PTL 1: JP 2007-326807 A

SUMMARY OF THE INVENTION

The present invention relates to the following [1] to [2].
[1] A hair cosmetic containing the following components (A) to (E):
(A) a compound represented by the following general formula (1) or a salt thereof:

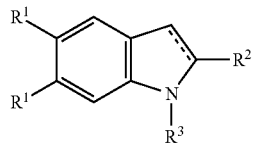

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;
(B) an alkaline agent;
(C) a buffering agent;
(D) an anionic surfactant; and
(E) a cationic polymer having a cation charge density of 0.01 meq/g or more and 4.8 meq/g or less,
a mass ratio of the component (A) to the component (E) [(A)/(E)] being 0.05 or more and less than 2.
[2] A dyeing method of hair including a step of applying the hair cosmetic as set forth in the above [1] on hair.

DETAILED DESCRIPTION OF THE INVENTION

[Hair Cosmetic]
The hair cosmetic of the present invention contains the following components (A) to (E):
(A) a compound represented by the following general formula (1) or a salt thereof:

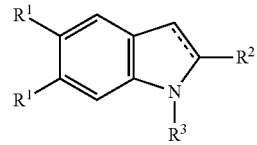

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;
(B) an alkaline agent;
(C) a buffering agent;
(D) an anionic surfactant; and
(E) a cationic polymer having a cation charge density of 0.01 meq/g or more and 4.8 meq/g or less,
a mass ratio of the component (A) to the component (E) [(A)/(E)] being 0.05 or more and less than 2.

It may not be said that the aforementioned melanin precursor-containing hair dye is satisfactory in hair dyeing properties as compared with typical oxidative hair dyes, and it is desired that the hair dyeing properties are more improved. In addition, though the technique disclosed in PTL 1 is a technique regarding the hair dye, during use of a hair dye, a lot of time and energy are spent, such that a care for preventing staining of a place where hair dyeing is carried out, such as a bathroom and a lavatory, is needed, so that it may not be said that the foregoing technique is a daily simply usable, and a long period of time is required in order to obtain a hair dyeing effect to some extent.

Then, the present inventors thought that by blending the aforementioned melanin precursor in a hair cosmetic, such as a shampoo which everyone uses in daily shampooing, high hair dyeing properties can be exhibited simply and for a short period of time, and made investigations.

However, for example, in shampooing, since a shampoo is applied and spread on hair wetted with water, components in the shampoo are greatly diluted. In addition, since the shampoo is one which washes away dirt attached onto the hair by using a surfactant or the like, it is very difficult to adsorb a sufficient amount of the melanin precursor onto the hair surface in order to exhibit high hair dyeing properties at the same time of cleansing the hair with the foregoing shampoo.

A problem of the present invention is to provide a hair cosmetic capable of simply obscuring gray hairs through a daily hair care behavior, such as shampooing, and exhibiting high hair dyeing properties.

The present inventors have found that the aforementioned problem can be solved by a hair cosmetic containing a predetermined melanin precursor, an alkaline agent, a buffering agent, an anionic surfactant, and a cationic polymer having a specified charge density in predetermined ratios.

In accordance with the hair cosmetic of the present invention, it is possible to simply obscure gray hairs through a daily hair care behavior, such as shampooing, and to obtain a high gray hair dyeing effect for a short period of time.

In the present invention, examples of the hair cosmetic include a hair conditioner, a hair treatment agent, and a hair dye, in addition to a hair cleansing agent, such as a shampoo.

Of these, a hair cleansing agent is preferred from the viewpoint of obtaining the effects of the present invention and the viewpoint of enabling one to simply achieve dyeing through a daily hair care behavior. The formulation of the hair cosmetic is not particularly limited, and it is possible to take an arbitrary formulation, for example, a liquid, a foam, a paste, a cream, a solid, and a powder. For example, in the case of a hair cleansing agent, the formulation is preferably a liquid, a paste, or a cream, and more preferably a liquid.

By daily using a hair cosmetic, such as the hair cleansing agent containing the aforementioned components (A) to (E), high hair dyeing properties can be obtained through a daily hair care behavior, such as shampooing.

In order to reveal high hair dyeing properties, it is preferred to adsorb a sufficient amount of the melanin precursor (component (A)) onto the hair surface. However, as mentioned above, for example, in the case of shampooing with a hair cleansing agent, such as a shampoo, since the shampoo is applied and spread on hair wetted with water, the components in the shampoo are greatly diluted. In addition, since the shampoo is one which washes away dirt attached onto the hair by using a surfactant or the like, it was very difficult to adsorb a sufficient amount of the melanin precursor onto the hair surface for performing hair dyeing of gray hairs for a short period of time at the same time of cleansing the hair.

The present inventors thought that even under the circumstances under which the aforementioned surfactant-containing hair cosmetic is greatly diluted with water during use, it is needed to efficiently adsorb the component (A) onto the hair surface and made investigations. By combining an anionic surfactant as the component (D) with a cationic polymer having a specified charge density as the component (E), when the hair cosmetic is diluted with water, coacervation is produced. As a result, it has been found that the component (A) that is the melanin precursor is not only included in a high concentration within the coacervation but also adsorbed in a high concentration onto the hair surface. In general, though the coacervation refers to a phenomenon in which a concentrated colloid sol is separated from a uniform solution, in the present invention, it refers to a phenomenon in which an anionic surfactant and a cationized polymer form a water-insoluble complex to cause phase separation.

In addition, as mentioned later, an optimum pH range exists in order that the component (A) may reveal high hair dyeing properties. By using a buffering agent as the component (C) in the hair cosmetic, even in the case where the hair cosmetic is diluted with water during use, it is easy to maintain the aforementioned pH range, and therefore, the high hair dyeing properties can be obtained.

<Component (A)>

The hair cosmetic of the present invention contains the component (A) that is a compound represented by the following general formula (1) or a salt thereof. The component (A) is a melanin precursor which is polymerized through air oxidation and converted into a melanin pigment and acts as a dyeing agent of hair.

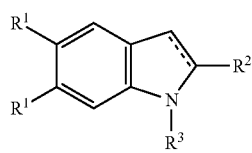

(1)

In the formula, a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group.

The melanin precursor of the component (A) is an indole derivative or an indoline derivative that is the compound represented by the general formula (1), or a salt thereof, and in the present invention, one or a combination of two or more thereof can be used. From the viewpoint of hair dyeing properties, the component (A) is more preferably an indole derivative (namely, a π bond exists in the broken line portion in the general formula (1)).

From the viewpoint of availability and hair dyeing properties of the component (A), in the general formula (1), $R^1$ is preferably a hydroxy group; $R^2$ is preferably a hydrogen atom or —COOR (R is a hydrogen atom, a methyl group, or an ethyl group), and more preferably a hydrogen atom or —COOH; and $R^3$ is preferably a hydrogen atom.

Examples of the compound represented by the general formula (1) include 5,6-dihydroxyindole, 5,6-dihydroxyindole-2-carboxylic acid, methyl 5,6-dihydroxyindole-2-carboxylate, ethyl 5,6-dihydroxyindole-2-carboxylate, N-methyl-5,6-dihydroxyindole, N-methyl-5,6-dihydroxyindole-2-carboxylic acid, N-ethyl-5,6-dihydroxyindole, N-ethyl-5,6-dihydroxyindole-2-carboxylic acid, N-acetyl-5,6-dihydroxyindole, N-acetyl-5,6-dihydroxyindole-2-carboxylic acid, 5-acetoxy-6-hydroxyindole, 5-acetoxy-6-hydroxyindole-2-carboxylic acid, 5,6-dihydroxyindoline, 5,6-dihydroxyindoline-2-carboxylic acid, methyl 5,6-dihydroxyindoline-2-carboxylate, ethyl 5,6-dihydroxyindoline-2-carboxylate, N-methyl-5,6-dihydroxyindoline, N-methyl-5,6-dihydroxyindoline-2-carboxylic acid, N-ethyl-5,6-dihydroxyindoline, N-ethyl-5,6-dihydroxyindoline-2-carboxylic acid, N-acetyl-5,6-dihydroxyindoline, N-acetyl-5,6-dihydroxyindoline-2-carboxylic acid, 5-acetoxy-6-hydroxyindoline, and 5-acetoxy-6-hydroxyindoline-2-carboxylic acid.

Examples of the salt of the compound represented by the general formula (1) include a hydrochloride, a hydrobromide, a sulfate, a phosphate, an acetate, a propionate, a lactate, and a citrate of the foregoing compounds. Above all, a hydrobromide is preferred from the viewpoint of availability.

In the general formula (1), when $R^2$ is —COOH, examples of the salt of the compound represented by the general formula (1) include carboxylates thereof (R is —COO$^-$X$^+$ (X$^+$ is a cation, such as an alkali metal ion, e.g., Na$^+$ and K$^+$, an alkaline earth metal ion, e.g., Ca$^+$ and Mg$^+$, and an ammonium ion)).

From the viewpoint of dyeing the hair in a natural color shade, the component (A) is preferably one or more selected from the group consisting of 5,6-dihydroxyindole, 5,6-dihydroxyindole-2-carboxylic acid, 5,6-dihydroxyindoline, and 5,6-dihydroxyindoline-2-carboxylic acid, and salts thereof; more preferably one or more selected from the group consisting of 5,6-dihydroxyindole, 5,6-dihydroxyindole-2-carboxylic acid, and 5,6-dihydroxyindoline hydrobromide; still more preferably one or two selected from the group consisting of 5,6-dihydroxyindole and 5,6-dihydroxyindole-2-carboxylic acid; and yet still more preferably a combination of 5,6-dihydroxyindole and 5,6-dihydroxyindole-2-carboxylicacid.

In the case of use of a combination of 5,6-dihydroxyindole and 5,6-dihydroxyindole-2-carboxylic acid, a molar ratio thereof is preferably in a range of 50/50 to 99/1, more preferably in a range of 80/20 to 99/1, and still more preferably in a range of 85/15 to 95/5. When the molar ratio of 5,6-dihydroxyindole to 5,6-dihydroxyindole-2-carboxylic acid falls within the aforementioned range, finish of the hair after hair dyeing becomes close to a natural color tint.

The molar ratio of 5,6-dihydroxyindole to 5,6-dihydroxyindole-2-carboxylic acid can be quantitatively determined by means of reversed phase HPLC.

From the viewpoint of improvement in hair dyeing properties, the content of the component (A) in the hair cosmetic is preferably 0.05% by mass or more, and more preferably 0.1% by mass or more, and from the viewpoint of economy, it is preferably 5% by mass or less, more preferably 3% by mass or less, still more preferably 1% by mass or less, and yet still more preferably 0.8% by mass or less.

<Component (B)>

The hair cosmetic of the present invention contains the component (B) that is an alkaline agent. The component (B) has not only an action to swell the hair, thereby opening the cuticle and penetrating a dyeing agent component, such as the component (A), into the interior of the hair, but also an action to promote a polymerization reaction of the component (A), thereby improving the hair dyeing properties. As the component (B), any material can be used without particular limitations so long as it is an alkaline agent that is used for usual hair dyes.

Examples of the alkaline agent include ammonia; alkanolamines, such as mono-, di-, or tri-methanolamine and mono-, di-, or tri-ethanolamine; alkylamines, such as methylamine, dimethylamine, ethylamine, diethylamine, N-methylethylamine, propylamine, and butylamine; aralkylamines, such as benzylamine; and inorganic alkaline compounds, such as sodium hydroxide and potassium hydroxide, and one or more of these materials can be used. The carbon number of the alkanolamine, alkylamine, or aralkylamine is preferably 10 or less, and more preferably 8 or less from the viewpoint of water solubility.

Above all, from the viewpoint of hair dyeing properties, the component (B) is preferably one or more selected from the group consisting of ammonia, an alkanolamine, an alkylamine, an aralkylamine, sodium hydroxide, and potassium hydroxide. The component (B) more preferably contains one or more of ammonia and an alkanolamine, still more preferably contains a monoalkanolamine, and yet still more preferably contains monoethanolamine.

From the viewpoint of obtaining high hair dyeing properties, the content of the component (B) in the hair cosmetic is preferably 0.01% by mass or more, more preferably 0.1% by mass or more, and still more preferably 0.5% by mass or more, and from the viewpoint of suppressing irritation, it is preferably 10% by mass or less, more preferably 5% by mass or less, and still more preferably 3% by mass or less.

<Component (C)>

The hair cosmetic of the present invention contains the component (C) that is a buffering agent. In view of the fact that the hair cosmetic contains the component (C), even in the case where the hair cosmetic is diluted with water during use, in order that the component (A) may reveal high hair dyeing properties, it is easy to maintain an optimum pH range.

Although the buffering agent is not particularly limited so long as it has a pH buffering action, since the component (A) that is the melanin precursor reacts with oxygen in air under a basic condition, whereby it is liable to be converted into a melanin pigment, a buffering agent capable of regulating the pH of the hair cosmetic to the basic condition is preferred.

From the aforementioned viewpoint, as for the component (C), a buffering agent containing, as a basic component, any one of a carbonate, such as sodium carbonate, potassium carbonate, sodium bicarbonate, and potassium bicarbonate, glycine, sodium tetraborate, and ammonium chloride, or a buffering agent composed of a combination of two or more basic components, such as sodium carbonate-sodium bicarbonate, is preferred; a buffering agent containing a carbonate is more preferred; and a buffering agent containing sodium bicarbonate is still more preferred.

From the viewpoint of improving a pH buffering ability, the component (C) may further contain a protonating agent as a buffering agent component. The protonating agent may be any of a monobasic acid and a polybasic acid, and may be any of an organic acid (the carbon number is 1 or more and 8 or less, provided that ascorbic acid is excluded) and an inorganic acid. As the protonating agent, one or more selected from the group consisting of hydrochloric acid, sulfuric acid, phosphoric acid, formic acid, acetic acid, and citric acid are exemplified, and one or two selected from the group consisting of phosphoric acid and citric acid are more preferred.

From the viewpoint of improvement in hair dyeing properties, the buffering agent component constituting the component (C) is still more preferably composed of a combination of sodium bicarbonate with one or two selected from the group consisting of phosphoric acid and citric acid.

Although the content of the component (C) in the hair cosmetic is not particularly limited so long as it is an amount at which the pH of the hair cosmetic can be regulated to a desired range, it is preferably 0.5% by mass or more, more preferably 1.0% by mass or more, and still more preferably 1.5% by mass or more from the viewpoint of improving a pH buffering ability in the case where the hair cosmetic is diluted with water. In addition, from the viewpoint of formulation stability, the content of the component (C) in the hair cosmetic is preferably 5.0% by mass or less, more preferably 4.0% by mass or less, and still more preferably 3.5% by mass or less.

The content of the component (C) means a sum total of the active components of the buffering agent components constituting the component (C).

<pH>

From the viewpoint of promoting the polymerization reaction of the component (A) and improving the hair dyeing properties, a pH of the hair cosmetic of the present invention is preferably 8.0 or more, more preferably 8.5 or more, and still more preferably 9.0 or more. This is because the component (A) that is the melanin precursor reacts with oxygen in air under a basic condition, whereby it is liable to be converted into a melanin pigment. From the viewpoint of improvement in hair dyeing properties and suppression of any damage to the hair, the foregoing pH is preferably 12.0 or less, more preferably 11.0 or less, still more preferably 10.5 or less, and yet still more preferably 10.0 or less.

The aforementioned pH is a measured value at 25° C., and specifically, it can be measured by a method described in the section of Examples.

<Component (D)>

The hair cosmetic of the present invention contains the component (D) that is an anionic surfactant. The component (D) has an action of not only giving a cleansing effect to the hair in the case where the hair cosmetic is a hair cleansing agent, but also producing coacervation in a system in which the hair cosmetic is diluted with water through a combination with a cationic polymer as the component (E) as mentioned later, whereby the component (A) is not only included in a high concentration within the coacervation but also adsorbed onto the hair surface, to reveal high hair dyeing properties.

Examples of the anionic surfactant include an alkylbenzene sulfonate, an alkyl or alkenyl ether sulfate, an alkyl or alkenyl sulfate, an olefin sulfonate, an alkane sulfonate, a saturated or unsaturated fatty acid salt, an alkyl or alkenyl ether carboxylate, an α-sulfo fatty acid salt, a N-acylamino acid, a phosphoric acid mono- or diester, and a sulfosuccinic acid ester. One or more of these anionic surfactants can be used.

Examples of a counter ion of an anionic group of the anionic surfactant include an alkali metal ion, such as a sodium ion and a potassium ion; an alkaline earth metal ion, such as a calcium ion and a magnesium ion; an ammonium ion; and an alkanolamine having 1 to 3 alkanol groups having 2 or 3 carbon atoms (for example, monoethanolamine, diethanolamine, triethanolamine, and triisopropanolamine).

Above all, from the viewpoint of favorable lathering, easiness for washing, and an improving effect for hair dyeing properties owing to coacervation formation in the case where the hair cosmetic is a hair cleansing agent, the component (D) is preferably one or more selected from the group consisting of an alkyl ether sulfate and an alkyl ether carboxylate. Examples of the alkyl ether sulfate include a polyoxyethylene alkyl ether sulfate, and examples of the alkyl ether carboxylate include a polyoxyethylene alkyl ether acetate.

From the viewpoint of favorable lathering, easiness for washing, and coacervation formation in the case where the hair cosmetic is a hair cleansing agent, the content of the component (D) in the hair cosmetic is preferably 3% by mass or more, more preferably 5% by mass or more, and still more preferably 8% by mass or more. In addition, from the viewpoint of improvement in hair dyeing properties and suppression of any damage to the hair, it is preferably 40% by mass or less, more preferably 30% by mass or less, still more preferably 20% by mass or less, and yet still more preferably 15% by mass or less.

<Component (E)>

The hair cosmetic of the present invention contains a cationic polymer having a cation charge density of 0.01 meq/g or more and 4.8 meq/g or less as the component (E). The component (E) has an action of not only producing coacervation through a combination with the component (D), whereby the component (A) is not only included in a high concentration within the coacervation but also adsorbed onto the hair surface, to reveal high hair dyeing properties.

In the present invention, the cationic polymer is one having a cationic group and refers to a water-soluble polymer exhibiting cationic properties as a whole. That is, as for the cationic polymer, in addition to a cationic polymer having only a cationic group and not having an anionic group, an ampholytic polymer having a cationic group and an anionic group and exhibiting cationic properties as a whole is also included in the cationic polymer of the present invention.

The anionic group refers to an anion group or a group which may be ionized to become an anion group.

In the present invention, (1) in the case of a cationic polymer having a cationic group and not having an anionic group, the cation charge density of the cationic polymer refers to [(molar number of the cationic group contained per 1 gram of the cationic polymer)×1,000 (meq/g)]. In addition, (2) in the case of a polymer having a cationic group and an anionic group, the polymer is needed to exhibit cationic properties as a whole. In this case, the cation charge density refers to a value obtained by subtracting [(molar number of the anionic group)×1,000 (anion charge density; meq/g)] from [(molar number of the cationic group)×1,000 (cation charge density; meq/g)]. A polymer in which the foregoing value is positive and falls within a range of 0.01 meq/g or more and 4.8 meq/g or less is included in the component (E).

In the hair cosmetic of the present invention, two or more cationic polymers may be used as the component (E). The cation charge density of this case is determined through calculation by weighted averaging of cation charge densities and blending amounts of the respective polymers.

The cation charge density of the component (E) is 0.01 meq/g or more and 4.8 meq/g or less, and from the viewpoint of improvement in hair dyeing properties, it is preferably 0.05 meq/g or more, more preferably 0.1 meq/g or more, still more preferably 0.2 meq/g or more, yet still more preferably 0.3 meq/g or more, and even yet still more preferably 0.4 meq/g or more, and it is preferably 4.7 meq/g or less, more preferably 4.0 meq/g or less, still more preferably 3.5 meq/g or less, yet still more preferably 3.0 meq/g or less, even yet still more preferably 2.5 meq/g or less, even still more preferably 2.0 meq/g or less, and even still more further preferably 1.5 meq/g or less.

Specifically, the cation charge density of the component (E) can be determined by a method described in the section of Examples.

The cationic polymer which is used for the component (E) can be used without particular limitations so long as it is a cationic polymer whose cation charge density falls within the aforementioned range, or it is a combination of two or more cationic polymers, in which the cation charge density thereof falls within the aforementioned range. From the viewpoint of improving the hair dyeing properties, it is preferred to use, as the component (E), one or a combination of two or more cationic polymers only, in which the cation charge density thereof falls within the aforementioned range.

Examples of the cationic polymer include a cationized guar gum; a cationized tara gum; a cationized locust bean gum; a cationized polyvinyl alcohol; a cationized cellulose; a cationized hydroxyalkyl cellulose, such as a cationized hydroxyethyl cellulose and a cationized hydroxypropyl cellulose; a cationic starch; a quaternized dialkylaminoalkyl (meth)acrylate polymer, such as a vinylpyrrolidone/N,N-dimethylaminoethyl methacrylate diethyl sulfate copolymer and a N,N-dimethylaminoethyl methacrylate diethyl sulfate/N,N-dimethyl acrylamide/dimethacrylic acid polyethylene glycol copolymer; a diallyl quaternized ammonium salt polymer, such as polydiallyldimethylammonium chloride, a diallyldimethylammonium chloride/acrylic acid copolymer, a diallyldimethylammonium chloride/acrylamide copolymer, and a diallyldimethylammonium chloride/acrylic acid/acrylamide copolymer; a vinyl imidazolium trichloride/vinylpyrrolidone copolymer; a vinylpyrrolidone/alkylamino (meth)acrylate copolymer; a vinylpyrrolidone/alkylamino (meth)acrylate/vinyl caprolactam copolymer; a vinylpyrrolidone/(meth)acrylamidopropyl trimethylammonium chloride copolymer; an alkyl acrylamide/(meth)acrylate/alkylaminoalkyl acrylamide/polyethylene glycol (meth)acrylate copolymer; an adipic acid/dimethylaminohydroxypropyl ethylene triamine copolymer; and cationic polymers described in JPS 53-139734 A and JPS 60-36407 A. These can be used alone or in combination of two or more thereof.

From the viewpoint that the coacervation is readily produced and that high hair dying properties can be revealed, the component (E) is preferably one or more selected from the group consisting of a cationized guar gum, a cationized tara gum, a cationized locust bean gum, a cationized polyvinyl alcohol, a cationized hydroxyethyl cellulose, a cationized hydroxypropyl cellulose, a vinylpyrrolidone/N,N-dimethylaminoethyl methacrylate diethyl sulfate copolymer, a N,N-dimethylaminoethyl methacrylate diethyl sulfate/N,N-dimethyl acrylamide/dimethacrylic acid polyethylene glycol copolymer, polydiallyldimethylammonium chloride, a diallyldimethylammonium chloride/acrylic acid copolymer, a diallyldimethylammonium chloride/acrylamide copolymer, and a diallyldimethylammonium chloride/acrylic acid/acrylamide polymer; more preferably one or more selected from the group consisting of a cationized guar gum, a cationized tara gum, a cationized polyvinyl alcohol, a cationized hydroxyethyl cellulose, a cationized hydroxypropyl cellulose, a N,N-dimethylaminoethyl methacrylate diethyl sulfate/N,N-dimethyl acrylamide/dimethacrylic acid polyethylene glycol copolymer, polydiallyldimethylammonium chloride, a diallyldimethylammonium chloride/acrylic acid copolymer, a diallyldimethylammonium chloride/acrylamide copolymer, and a diallyldimethylammonium chloride/acrylic acid/acrylamide polymer; and still more preferably one or more selected from the group consisting of a cationized guar gum, a cationized tara gum, a cationized polyvinyl alcohol, a cationized hydroxyethyl cellulose, a cationized hydroxypropyl cellulose, a N,N-dimethylaminoethyl methacrylate diethyl sulfate/N,N-dimethyl acrylamide/dimethacrylic acid polyethylene glycol copolymer, a diallyldimethylammonium chloride/acrylic acid copolymer, and a diallyldimethylammonium chloride/acrylamide copolymer.

Examples of a commercially available cationic polymer which can be uses alone or in combination of two or more thereof as the component (E) include those described below.
(Cationized Guar Gum)
JAGUAR EXCEL: cation charge density=1.1 meq/g (manufactured by Solvay (Novecare)), etc.
(Cationized Tara Gum)
CATINAL CTR-100: cation charge density=1.3 meq/g (manufactured by Toho Chemical Industry Co., Ltd.), etc.
(Cationized Locust Bean Gum)
CATINAL CLB-100 (manufactured by Toho Chemical Industry Co., Ltd.), etc.
(Cationized Polyvinyl Alcohol)
GOHSENX K-434 (manufactured by The Nippon Synthetic Chemical Industry Co., Ltd., CM318: cation charge density=0.35 meq/g (manufactured by Kuraray Co., Ltd.), etc.
(Cationized Hydroxyethyl Cellulose)
Polyquaternium-10 (o-[2-hydroxy-3-(trimethylammonio)propyl]hydroxyethyl cellulose chloride): for example, UCARE POLYMER JR-400: cation charge density=1.3 meq/g (manufactured by The Dow chemical Company), POISE C-60H: cation charge density=1.1 to 1.8 meq/g (manufactured by Kao corporation), POISE C-150L: cation charge density=0.7 to 1.1 meq/g (manufactured by Kao corporation), and CATICELO M-80: cation charge density=1.0 meq/g (manufactured by Kao Corporation)
(Cationized hydroxypropyl cellulose)
SOFCARE C-HP2: cation charge density=0.5 meq/g (manufactured by Kao Corporation), etc. (Vinylpyrrolidone/N,N-dimethylaminoethyl methacrylate diethyl sulfate copolymer)
Polyquaternium-11: for example, GAFQUAT 734 (manufactured by ISP Japan Ltd.), GAFQUAT 755N (manufactured by ISP Japan Ltd.), etc. (N,N-Dimethylaminoethyl methacrylate diethyl sulfate/N,N-dimethyl acrylamide/dimethacrylic acid polyethylene glycol copolymer)

Polyquaternium-52: for example, SOFCARE KG-101W-E: cation charge density (literature value)=0.8 meq/g (manufactured by Kao Corporation), etc.
Polyquaternium-6: for example, MERQUAT 100: cation charge density (literature value)=6.2 meq/g (manufactured by Lubrizol Advanced Materials), etc.
(Diallyldimethylammonium Chloride/Acrylic Acid Copolymer)
Polyquaternium-22: for example, MERQUAT 280: cation charge density=2.2 meq/g and MERQUAT 295: cation charge density=5.7 meq/g (all of which are manufactured by Lubrizol Advanced Materials), etc.
(Diallyldimethylammonium Chloride/Acrylamide Copolymer)
Polyquaternium-7: for example, MERQUAT 550: cation charge density (literature value)=3.1 meq/g (manufactured by Lubrizol Advanced Materials), etc.
(Diallyldimethylammonium Chloride/Acrylic Acid/Acrylamide Polymer)
Polyquaternium-39: for example, MERQUAT 3331PR: cation charge density=0.42 meq/g (manufactured by Lubrizol Advanced Materials), etc.

From the viewpoint of improvement in hair dyeing properties, the content of the component (E) in the hair cosmetic is preferably 0.05% by mass or more, more preferably 0.1% by mass or more, still more preferably 0.2% by mass or more, and yet still more preferably 0.3% by mass or more. In addition, from the viewpoint of improvement in stability and improvement in hair dyeing properties, the foregoing content is preferably 5% by mass or less, more preferably 3% by mass or less, still more preferably 1.5% by mass or less, yet still more preferably 1% by mass or less, and even yet still more preferably 0.6% by mass or less.

From the viewpoint of improvement in hair dyeing properties and improvement in stability, a mass ratio of the component (A) to the component (E) [(A)/(E) in the hair cosmetic is 0.05 or more, preferably 0.1 or more, more preferably 0.15 or more, still more preferably 0.2 or more, and yet still more preferably 0.25 or more. On the other hand, from the viewpoint of efficacy in the case where the hair cosmetic is a hair cleansing agent (improvements in hair dyeing properties and resistance to washing), the mass ratio of the component (A) to the component (E) [(A)/(E)] is less than 2, preferably 1.95 or less, more preferably 1.8 or less, still more preferably 1.7 or less, yet still more preferably 1.6 or less, even yet still more preferably 1.5 or less, even still more preferably 1.4 or less, even still more further preferably 1.2 or less, and even yet still more further preferably 1.0 or less.

<Component (F)>

It is preferred that the hair cosmetic further contains at least one polymer selected from the group consisting of polyvinyl alcohol and polyvinylpyrrolidone (hereinafter also referred to as "component (F)") as a polymer other than the component (E). In view of the fact that the hair cosmetic contains the component (F), the dyeing properties are more improved. Above all, from the viewpoint of improvement in dyeing properties, the component (F) is preferably polyvinyl alcohol.

From the viewpoint of improvement in hair dyeing properties, an average degree of polymerization of the component (F) is preferably 200 or more, more preferably 500 or more, still more preferably 700 or more, yet still more preferably 1,500 or more, and even yet still more preferably 1,900 or more. On the other hand, from the viewpoint of solubility in the hair cosmetic, the foregoing average degree of polymerization is preferably 10,000 or less, more preferably 7,000 or less, and still more preferably 3,000 or less.

As the component (F), two or more polymers may be used. In that case, the average degree of polymerization of the component (F) is determined by calculating a weighted average from the average degrees of polymerization and blending amounts of the respective polymers.

In the case where the component (F) is polyvinyl alcohol, though a degree of saponification of polyvinyl alcohol is not particularly limited, it is preferably 70% or more, and it is preferably 95% or less, and more preferably 90% or less, from the viewpoint of improvement in hair dyeing properties and handling properties during blending in the hair cosmetic.

As for the polyvinyl alcohol, one having a cationic group is excluded.

In the case of using the component (F), from the viewpoint of improvement in hair dyeing properties, the content thereof in the hair cosmetic is preferably 0.01% by mass or more, more preferably 0.05% by mass or more, still more preferably 0.10% by mass or more, and yet still more preferably 0.12% by mass or more. On the other hand, from the viewpoint of improvement in blending stability, the foregoing content is preferably 40% by mass or less, more preferably 10% by mass or less, still more preferably 5.0% by mass or less, yet still more preferably 2.0% by mass or less, and even yet still more preferably 1.0% by mass or less.

<Other Components>

The hair cosmetic of the present invention may appropriately contain, in addition to the aforementioned components, a component which is usually used for hair cosmetics or hair dyes, within a range where the purpose of the present invention is not impaired. Examples of the foregoing component include an ampholytic surfactant, an antioxidant, a silicone, an aromatic alcohol, a dyeing agent other than the component (A), a polymer other than the components (E) and (F), an oil, an anti-dandruff agent, a vitamin compound, a disinfectant, an antiinflammatory agent, an antiseptic, a chelating agent, a humectant, a pearlescent agent, a ceramide, a perfume, and an ultraviolet absorber.

(Ampholytic Surfactant)

Examples of the ampholytic surfactant include a betaine-based surfactant, such as an alkyl dimethyl amino acetic acid betaine, a fatty acid amide propyl betaine, and an alkylhydroxy sulfobetaine; and a sultaine-based surfactant, such as lauryl hydroxysultaine. Above all, from the viewpoint of adaptability to hair and favorable lathering, a betaine-based surfactant is preferred, and a fatty acid amide propyl betaine is more preferred. The fatty acid amide propyl betaine is preferably one having an acyl group having 8 or more and 18 or less carbon atoms, and moreover, 10 or more and 16 or less carbon atoms, and one or more selected from the group consisting of lauric acid amide propyl betaine, a palm kernel oil fatty acid amide propyl betaine, and a coconut oil fatty acid amide propyl betaine are preferred.

In the case of using an ampholytic surfactant, from the viewpoint of adaptability to hair and favorable lathering, the content thereof in the hair cosmetic is preferably 0.05% by mass or more, more preferably 0.10% by mass or more, still more preferably 0.15% by mass or more, yet still more preferably 0.50% by mass or more, and even yet still more preferably 1.0% by mass or more, and it is preferably 15% by mass or less, more preferably 12% by mass or less, and still more preferably 10% by mass or less.

(Antioxidant)

Examples of the antioxidant include sulfurous acid, ascorbic acid, thioglycolic acid, L-cysteine, and N-acetyl-L-cysteine, and salts thereof. From the viewpoint of stabilization of the component (A) and improvement in dyeing properties, ascorbic acid and a salt thereof are preferred.

In the case of using the antioxidant, the content thereof in the hair cosmetic is preferably 0.05% by mass or more, and more preferably 0.1% by mass or more, and it is preferably 10% by mass or less, more preferably 5% by mass or less, and still more preferably 2% by mass or less.

(Silicone)

For example, in the case where the hair cosmetic is a hair cleansing agent, the silicone has an effect for improving foam texture, foam slipperiness, crease reduction during cleansing, and smoothness during drying. Examples of the silicone include dimethyl polysiloxane; methylphenyl polysiloxane; an amino-modified silicone, such as amodimethicone, aminoethylaminopropyl dimethicone, and aminopropyl dimethicone; a cyclic silicone; a polyether-modified silicone; a fatty acid-modified silicone; an alcohol-modified silicone; an alkoxy-modified silicone; an epoxy-modified silicone; a fluorine-modified silicone; and an alkyl-modified silicone. One or more of these silicones can be contained.

Above all, dimethyl polysiloxane is preferred as the silicone from the viewpoint of improving foam texture, foam slipperiness, crease reduction during cleansing, and smoothness during drying.

In the case of using the silicone, the content thereof in the hair cosmetic is preferably 0.1% by mass or more, more preferably 0.2% by mass or more, still more preferably 0.5% by mass or more, and yet still more preferably 2% by mass or more from the viewpoint of improving foam texture, foam slipperiness, crease reduction during cleansing, and smoothness during drying, and it is preferably 15% by mass or less, more preferably 10% by mass or less, and still more preferably 8% by mass or less from the viewpoint of improving foam texture, foam slipperiness, crease reduction during cleansing, and smoothness during drying and the viewpoint of economy.

(Aromatic Alcohol)

From the viewpoint of solubility of the component (E), the hair cosmetic of the present invention may further contain an aromatic alcohol. Examples of the aromatic alcohol include benzyloxyethanol, benzyl alcohol, phenethyl alcohol, γ-phenylpropyl alcohol, cinnamic alcohol, anise alcohol, p-methylbenzyl alcohol, α,α-dimethylphenethyl alcohol, α-phenyl ethanol, and phenoxyethanol. Of these, one or more selected from the group consisting of benzyloxyethanol and benzyl alcohol are preferred, and benzyl alcohol is more preferred.

In the case of using the aromatic alcohol, from the viewpoint of solubility of the component (E), the content thereof in the hair cosmetic is preferably 0.05% by mass or more, and more preferably 0.1% by mass or more, and it is preferably 5% by mass or less, more preferably 3% by mass or less, and still more preferably 2% by mass or less.

(Dyeing Agent Other than Component (A))

The hair cosmetic of the present invention may further contain a dyeing agent other than the component (A). Examples of the foregoing dyeing agent include an oxidation dye (constituted of a precursor and a coupler) and a direct dye, each of which is typically used for hair dyes.

As the dying agent other than the component (A), one or more materials can be used. The foregoing dyeing agent is preferably an oxidation dye. As the precursor, paraphenylenediamine, toluene-2,5-diamine, paraaminophenol, 4-aminometacresol, 1-hydroxyethyl-4,5-diaminopyrazole, and salts thereof are preferred; and as the coupler, 2,4-diaminophenoxyethanol, metaaminophenol, 2-methyl-5- aminophenol, resorcin, 2-methylresorcin, 4-chlororesorcinol, 1-naphthol, 2-amino-3-hydroxypyridine, 2-amino-4-(8-hydroxy)aminoanisole, and salts thereof are preferred.

In the case of using the dyeing agent other than the component (A), the content thereof in the hair cosmetic is preferably 0.01% by mass or more, and more preferably 0.05% by mass or more from the viewpoint of improvement in hair dyeing properties, and it is preferably 1% by mass or less, and more preferably 0.5% by mass or less from the viewpoint of obtaining a natural color shade through hair dyeing with the component (A).

(Aqueous Medium)

The hair cosmetic typically contains an aqueous medium. Examples of the aqueous medium include water; a lower alcohol, such as ethanol and isopropyl alcohol; and a low-molecular diol or triol having 6 or less carbon atoms, such as 1,3-butylene glycol, glycerin, ethylene glycol, and propylene glycol, with water being preferred. Although the content of the aqueous medium in the hair cosmetic can be appropriately selected depending upon the formulation of the hair cosmetic, it is typically in a range of 1 to 95% by mass. In the case of using water as the aqueous medium, from the viewpoint that when the hair cosmetic is diluted with water during use, coacervation is produced, and the component (A) is adsorbed onto the hair surface, thereby revealing high hair dyeing properties, the content of water in the hair cosmetic is preferably 50% by mass or more, more preferably 60% by mass or more, and still more preferably 70% by mass, and it is preferably 95% by mass or less, and more preferably 90% by mass or less.

A production method of the hair cosmetic of the present invention is not particularly limited. For example, the hair cosmetic of the present invention can be produced by blending the components (A) to (E), and other components which are used, if desired by a method described in the section of Examples and mixing the blend by using a known stirring device or the like.

[Dyeing Method of Hair]

The present invention further provides a dyeing method of hair including a step of applying the aforementioned hair cosmetic on hair. For example, in the case where the hair cosmetic is a hair cleansing agent, such as a shampoo, the hair cleansing agent is applied on hair, lathered to cleanse the hair, and then rinsed away with water. In the case where the hair cosmetic is a hair conditioning agent, a hair treatment agent, or a hair dye, the hair cosmetic is applied on hair, optionally allowed to stand for a short time (about 1 to 5 minutes), and then rinsed away with water. By daily repeating such a step, gray hair dyeing can be performed easily and within a short period of time.

Regarding the aforementioned embodiments, the present invention discloses the following hair cosmetics and dyeing methods of hair.

<1> A hair cosmetic containing the following components (A) to (E):

(A) 0.05% by mass or more and 2% by mass or less of a compound represented by the following general formula (1) or a salt thereof:

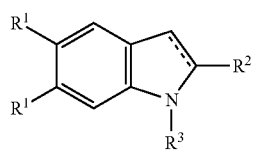

wherein a broken line represents the presence or absence of a n bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) an alkaline agent;
(C) a buffering agent;
(D) an anionic surfactant; and
(E) 0.1% by mass or more and 3% by mass or less of a cationic polymer having a cation charge density of 0.01 meq/g or more and 4.8 meq/g or less, a mass ratio of the component (A) to the component (E) [(A)/(E)] being 0.05 or more and less than 2.

<2> A hair cosmetic containing the following components (A) to (E):

(A) 0.05% by mass or more and 2% by mass or less of a compound represented by the following general formula (1) or a salt thereof:

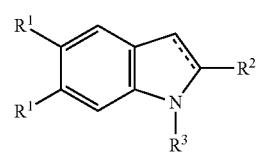

wherein a broken line represents the presence or absence of a n bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) an alkaline agent;
(C) a buffering agent;
(D) 5% by mass or more and 30% by mass or less of an anionic surfactant; and
(E) 0.05% by mass or more and 3.0% by mass or less of a cationic polymer having a cation charge density of 0.01 meq/g or more and 4.8 meq/g or less, a mass ratio of the component (A) to the component (E) [(A)/(E)] being 0.05 or more and 1.5 or less.

<3> A hair cosmetic containing the following components (A) to (E):

(A) 0.1% by mass or more and 2% by mass or less of a compound represented by the following general formula (1) or a salt thereof:

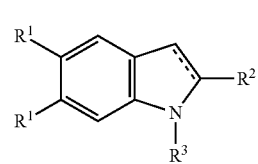

wherein a broken line represents the presence or absence of a n bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) 0.5% by mass or more and 5% by mass or less of an alkaline agent;

(C) 1.0% by mass or more and 4.0% by mass or less of a buffering agent;

(D) 5% by mass or more and 30% by mass or less of an anionic surfactant; and (E) 0.1% by mass or more and 1.5% by mass or less of a cationic polymer having a cation charge density of 0.05 meq/g or more and 2.5 meq/g or less, a mass ratio of the component (A) to the component (E) [(A)/(E)] being 0.05 or more and 1.5 or less.

<4> A hair cosmetic containing the following components (A) to (E):

(A) 0.1% by mass or more and 2% by mass or less of a compound represented by the following general formula (1) or a salt thereof:

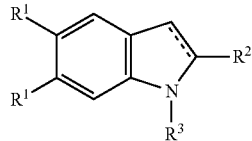

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) 0.5% by mass or more and 5% by mass or less of an alkaline agent;

(C) 1.0% by mass or more and 3.5% by mass or less of a buffering agent;

(D) 5% by mass or more and 20% by mass or less of an anionic surfactant;

(E) 0.1% by mass or more and 1% by mass or less of a cationic polymer having a cation charge density of 0.1 meq/g or more and 2.5 meq/g or less; and 60% by mass or more and 90% by mass or less of water, a mass ratio of the component (A) to the component (E) [(A)/(E)] being 0.05 or more and 1.0 or less.

<5> The hair cosmetic as set forth in any one of <1> to <4>, wherein the component (B) is selected from the group consisting of ammonia, an alkanolamine, an alkylamine, an aralkylamine, sodium hydroxide, and potassium hydroxide.

<6> The hair cosmetic as set forth in any one of <1> to <5>, wherein the component (B) contains one or more selected from the group consisting of ammonia and an alkanolamine.

<7> The hair cosmetic as set forth in any one of <1> to <6>, wherein the component (B) contains a monoalkanolamine.

<8> The hair cosmetic as set forth in any one of <1> to <7>, wherein the component (B) contains monoethanolamine.

<9> The hair cosmetic as set forth in any one of <1> to <8>, wherein the component (C) contains one or more basic components selected from sodium carbonate, potassium carbonate, sodium bicarbonate, potassium bicarbonate, glycine, sodium tetraborate, and ammonium chloride.

<10> The hair cosmetic as set forth in any one of <1> to <8>, wherein the component (C) contains a carbonate.

<11> The hair cosmetic as set forth in any one of <1> to <10>, wherein the component (C) contains sodium bicarbonate.

<12> The hair cosmetic as set forth in any one of <1> to <11>, wherein the component (C) contains one or more protonating agents selected from the group consisting of hydrochloric acid, sulfuric acid, phosphoric acid, formic acid, acetic acid, and citric acid.

<13> The hair cosmetic as set forth in any one of <1> to <12>, wherein the component (C) contains one or two protonating agents selected from the group consisting of phosphoric acid and citric acid.

<14> The hair cosmetic as set forth in any one of <1> to <8>, wherein the component (C) contains one or more basic components selected from sodium carbonate, potassium carbonate, sodium bicarbonate, potassium bicarbonate, glycine, sodium tetraborate, and ammonium chloride; and one or more protonating agents selected from the group consisting of hydrochloric acid, sulfuric acid, phosphoric acid, formic acid, acetic acid, and citric acid.

<15> The hair cosmetic as set forth in any one of <1> to <8>, wherein the component (C) contains one or more basic components selected from carbonates; and one or more protonating agents selected from the group consisting of phosphoric acid and citric acid.

<16> The hair cosmetic as set forth in any one of <1> to <8>, wherein the component (C) contains sodium bicarbonate and one or more selected from the group consisting of phosphoric acid and citric acid.

<17> The hair cosmetic as set forth in any one of <1> to <16>, wherein the component (D) contains one or more selected from the group consisting of an alkyl ether sulfate and an alkyl ether carboxylate.

<18> The hair cosmetic as set forth in any one of <1> to <17>, wherein the component (D) contains one or more selected from the group consisting of a polyoxyethylene alkyl ether sulfate and a polyoxyethylene alkyl ether acetate.

<19> The hair cosmetic as set forth in any one of <1> to <18>, wherein the component (E) contains one or more selected from the group consisting of a cationized guar gum, a cationized tara gum, a cationized locust bean gum, a cationized polyvinyl alcohol, a cationized hydroxyethyl cellulose, a cationized hydroxypropyl cellulose, a vinylpyrrolidone/N,N-dimethylaminoethyl methacrylate diethyl sulfate copolymer, a N,N-dimethylaminoethyl methacrylate diethyl sulfate/N,N-dimethyl acrylamide/dimethacrylic acid polyethylene glycol copolymer, polydiallyldimethylammonium chloride, a diallyldimethylammonium chloride/acrylic acid copolymer, a diallyldimethylammonium chloride/acrylamide copolymer, and a diallyldimethylammonium chloride/acrylic acid/acrylamide polymer.

<20> The hair cosmetic as set forth in any one of <1> to <19>, wherein the component (E) contains one or more selected from the group consisting of a cationized guar gum, a cationized tara gum, a cationized polyvinyl alcohol, a cationized hydroxyethyl cellulose, a cationized hydroxypropyl cellulose, a N,N-dimethylaminoethyl methacrylate diethyl sulfate/N,N-dimethyl acrylamide/dimethacrylic acid polyethylene glycol copolymer, polydiallyldimethylammonium chloride, a diallyldimethylammonium chloride/acrylic acid copolymer, a diallyldimethylammonium chloride/acrylamide copolymer, and a diallyldimethylammonium chloride/acrylic acid/acrylamide polymer.

<21> The hair cosmetic as set forth in any one of <1> to <20>, wherein the component (E) contains one or more selected from the group consisting of a cationized guar gum, a cationized tara gum, a cationized polyvinyl alcohol, a cationized hydroxyethyl cellulose, a cationized hydroxypropyl cellulose, a N,N-dimethylaminoethyl methacrylate diethyl sulfate/N,N-dimethyl acrylamide/dimethacrylic acid polyethylene glycol copolymer, a diallyldimethylammonium chloride/acrylic acid copolymer, and a diallyldimethylammonium chloride/acrylamide copolymer.

<22> The hair cosmetic as set forth in anyone of <1> to <21>, wherein a pH is 8.0 or more and 12.0 or less.
<23> The hair cosmetic as set forth in any one of <1> to <22>, wherein a pH is 8.5 or more and 11.0 or less.
<24> The hair cosmetic as set forth in any one of <1> to <23>, wherein a pH is 9.0 or more and 10.0 or less.
<25> The hair cosmetic as set forth in any one of <1> to <24>, further containing at least one polymer selected from the group consisting of polyvinyl alcohol and polyvinylpyrrolidone as a component (F).
<26> The hair cosmetic as set forth in any one of <1> to <25>, which is a hair cleansing agent.
<27> A dyeing method of hair including a step of applying the hair cosmetic as set forth in any one of <1> to <26> on hair.

EXAMPLES

The present invention is hereunder described by reference to Examples, but it should be construed that the present invention is not limited to the scope of the Examples. In the present Examples, the measurement of cation charge density, nitrogen content, and pH were performed by the following methods.

[Measurement of Cation Charge Density]

The cation charge density of a cationic polymer having only a cationic group and not having an anionic group was calculated according to the following expression (1) unless other specifically mentioned.

$$\text{Cation charge density (meq/g)} = [\text{Nitrogen content (\% by mass)}] \div 14 \times 10 \quad (1)$$

In addition, the cation charge density of a cationic polymer having a cationic group and an anionic group and exhibiting cationic properties as a whole was calculated according to the following expression (2) unless other specifically mentioned.

$$\text{Cation charge density (meq/g)} = [\text{Nitrogen content (\% by mass)}] \div 14 \times 10 - [\text{Anion charge density (meq/g)}] \quad (2)$$

In the expressions (1) and (2), the nitrogen content (% by mass) was measured by the Kjeldahl method as mentioned below. In addition, in the case where nitrogen other than the nitrogen of the quaternary ammonium cation is contained in the polymer, the cation charge density was determined while defining a value obtained by multiplying the nitrogen content determined by the Kjeldahl method as mentioned below by a value of [(nitrogen number of quaternary ammonium cation)/(total nitrogen number)] as the nitrogen content in the expression (1) and expression (2).

In addition, the anion charge density in the expression (2) was determined through calculation of the mmol number of a structural unit derived from a monomer having an anionic group in 1 g of the polymer through calculation from a mass ratio of a portion occupied by the structural unit derived from the monomer having an anionic group in the polymer.

[Measurement Method of Nitrogen Content (% by mass)]
(Kjeldahl Method) 100 mg of a cationic polymer which had been purified and dried, if desired was accurately metered, to which were then added 10 mL of sulfuric acid and one tablet of (5 g) of a decomposition accelerator (a Kjedahl tablet, manufactured by Merck), and then, complete decomposition was performed with a Kjeldahl decomposition apparatus ("K-432", manufactured by BUCHI) while undergoing temperature rise at 250° C. for 30 minutes, at 300° C. for 30 minutes, and at 420° C. for 80 minutes in this order. After completion of decomposition, 30 mL of ion-exchanged water was added to the sample. Using an automatic Kjeldahl distillation and titration apparatus ("K-370", manufactured by BUCHI), 40 mL of a 30% sodium hydroxide aqueous solution was added to make the sample alkaline, and then, ammonia liberated by means of a distillation operation was collected in a 1% boric acid aqueous solution, followed by titration with 0.01N sulfuric acid (for quantitative analysis, manufactured by Wako Pure Chemical Industries, Ltd.) to determine the nitrogen content (% by mass) in the cationic polymer.

[pH Measurement]

A pH at 25° C. of the hair cosmetic was measured with a pH meter (F-51, manufactured by HORIBA, Ltd.).

Preparation of Hair Cosmetic (Shampoo)

Examples 1 to 31 and Comparative Examples 1 and 4

According to each of compositions shown in Tables 1 to 5, an anionic surfactant and a part of water were mixed to prepare an aqueous solution, and then, a cationic polymer was dissolved therein. Furthermore, an alkaline agent, a buffering agent, and other components than ascorbic acid and an ampholytic surfactant among other components were added, and then, ascorbic acid and a solution of the component (A), and optionally, an ampholytic surfactant were added in a nitrogen atmosphere, to prepare a hair cosmetic. All of the hair cosmetics had a pH of 9.6.

Each of the prepared hair cosmetics was stored in a nitrogen atmosphere and dispersed on each occasion of evaluation of hair dyeing properties, and the following evaluation was carried out.

Comparative Examples 2 and 3

According to each of compositions shown in Tables 1 and 2, hair cosmetics were prepared in the same manner as mentioned above, except that the cationic polymer was not used. All of the hair cosmetics had a pH of 9.6.

[Evaluation of Hair Dyeing Properties]

For the evaluation of hair dyeing properties, a gray hair tress of a Chinese woman having a length of 10 cm and a mass of 1 g (BM-W-A, manufactured by Beaulax Co., Ltd.) was used. The hair tress for evaluation was previously cleansed twice with a plain shampoo having a composition shown below and air-dried, and then subjected to the following evaluation of hair dyeing properties.

| (Plain Shampoo) | (% by mass) |
|---|---|
| Sodium polyoxyethylene lauryl ether sulfate: (EMAL E-27C (active component amount: 27% by mass), manufactured by Kao Corporation) | 57.4 |
| Lauramide DEA: (AMINON L-02, manufactured by Kao Corporation) | 1.5 |
| EDTA-2Na: (FROST DS, manufactured by Daiichi Pure Chemical Co., Ltd.) | 0.3 |
| Phosphoric acid (adjusted at a pH of 7.0) | |
| Sodium benzoate | 0.5 |
| Purified water | Remainder |
| Total | 100 |

On the tress which had been rinsed with warm water for 20 seconds in advance, 0.1 g of the hair cosmetic obtained in each of the Examples was uniformly applied in a bath ratio of 1/1/0.1 (tress/water/hair cosmetic) and then lathered for 1 minute. Subsequently, the applied hair cosmetic was washed away with running warm water for 30 seconds, followed by drying with a towel and then drying with a dryer. This operation was repeated 3 times, 6 times, or 15 times, thereby carrying out a hair dyeing treatment.

A hue (L*, a*, b*) of each of the gray hair tress before the hair dyeing treatment and the tress after the hair dyeing treatment was measured at 6 points per tress by using a color color-difference meter (CR-400, manufactured by Konica Minolta, Inc.), and a color difference ΔE was calculated according to the following expression (3). It is evaluated that the larger the value of ΔE, the more favorable the hair dyeing properties.

$$\Delta E = [(\Delta L^*)^2 + (\Delta a^*)^2 + (\Delta b^*)^2]^{1/2} \quad (3)$$

(Δ: Amount of change of each hue before and after hair dyeing)

TABLE 1

|   |   |   | Example |   |   |   |   |   | Comparative Example |   |
|---|---|---|---|---|---|---|---|---|---|---|
|   |   |   | 1 | 2 | 3 | 4 | 5 | 6 | 1 | 2 |
| (A) | Compound represented by the general formula (1) or its salt | (A1) 5,6-Dihydroxyindole solution *1 | 15.00 | 15.00 | 15.00 | 15.00 | 15.00 | 15.00 | 15.00 | 15.00 |
| (B) | Alkaline agent | Monoethanolamine | 1.50 | 1.50 | 1.50 | 1.50 | 1.50 | 1.50 | 1.50 | 1.50 |
| (C) | Buffering agent | Sodium bicarbonate | 2.00 | 2.00 | 2.00 | 2.00 | 2.00 | 2.00 | 2.00 | 2.00 |
|   |   | Phosphoric acid (75%) *2 | 0.31 | 0.31 | 0.31 | 0.31 | 0.31 | 0.31 | 0.31 | 0.31 |
| (D) | Anionic surfactant | POE lauryl ether sulfuric acid Na (27.0%) *3 | 44.4 | 44.4 | 44.4 | 44.4 | 44.4 | 44.4 | 44.4 | 44.4 |
|   |   | POE lauryl ether acetic acid Na (18.2%) *4 |   |   |   |   |   |   |   |   |
| (E) | Cationic polymer (cation charge density: meq/g) | Polyquaternium-7 *5 (3.1) | 0.30 |   |   |   |   |   |   |   |
|   |   | Polyquaternium-10 *6 (1.0) |   | 0.30 |   |   |   |   |   |   |
|   |   | Polyquaternium-52 *7 (0.8) |   |   | 0.30 |   | 0.22 | 0.08 |   |   |
|   |   | Polyquaternium-22 *8 (2.2) |   |   |   | 0.30 |   |   |   |   |
|   |   | Polyquaternium-6 *9 (6.2) |   |   |   |   | 0.08 | 0.22 | 0.30 |   |
|   | Cation charge density of the whole of component (E) (meq/g) |   | 3.1 | 1.0 | 0.8 | 2.2 | 2.2 | 4.7 | 6.2 | — |
| Others | Ascorbic acid |   | 0.20 | 0.20 | 0.20 | 0.20 | 0.20 | 0.20 | 0.20 | 0.20 |
|   | Water |   | 36.29 | 36.29 | 36.29 | 36.29 | 36.29 | 36.29 | 36.29 | 36.59 |
| Total |   |   | 100.0 | 100.0 | 100.0 | 100.0 | 100.0 | 100.0 | 100.0 | 100.0 |
| (A)/(E) mass ratio |   |   | 0.57 | 0.57 | 0.57 | 0.57 | 0.57 | 0.57 | 0.57 | — |
| Evaluation ΔE | Hair dyeing: 3 times |   | 13.1 | 14.0 | 14.4 | 13.9 | 12.6 | 12.4 | 9.7 | 13.6 |
|   | Hair dyeing: 6 times |   | 21.1 | 23.8 | 21.9 | 21.6 | 20.2 | 20.2 | 17.7 | 19.6 |

TABLE 2

|   |   |   | Example |   |   |   |   |   |   |   |   |
|---|---|---|---|---|---|---|---|---|---|---|---|
|   |   |   | 7 | 8 | 9 | 10 | 11 | 12 | 13 | 14 | 15 |
| (A) | Compound represented by the general formula (1) or its salt | (A1) 5,6-Dihydroxyindole solution *1 | 15.00 | 15.00 | 15.00 | 15.00 | 15.00 | 15.00 | 15.00 | 15.00 | 15.00 |
| (B) | Alkaline agent | Monoethanolamine | 1.50 | 1.50 | 1.50 | 1.50 | 1.50 | 1.50 | 1.50 | 1.50 | 1.50 |
| (C) | Buffering agent | Sodium bicarbonate | 2.00 | 2.00 | 2.00 | 2.00 | 2.00 | 2.00 | 2.00 | 2.00 | 2.00 |
|   |   | Phosphoric acid (75%) *2 | 0.31 | 0.31 | 0.31 |   | 0.31 | 0.31 | 0.31 | 0.31 | 0.31 |
|   |   | Citric acid |   |   |   | 0.50 |   |   |   |   |   |
| (D) | Anionic surfactant | POE lauryl ether sulfuric acid Na (27.0%) *3 | 44.40 | 44.40 | 44.40 | 44.40 | 44.40 | 39.60 | 39.60 | 44.40 | 44.40 |
|   |   | POE lauryl ether acetic acid Na (18.2%) *4 |   |   |   |   |   |   | 7.70 | 7.70 |   |   |
| (E) | Cationic polymer (cation charge density: meq/g) | Cationized guar gum *10 (1.1) | 0.30 |   |   |   |   |   |   | 0.10 | 0.60 |
|   |   | Cationized tara gum *11 (1.3) |   | 0.30 |   |   |   | 0.30 | 0.30 |   |   |
|   |   | Cationized PVA *12 (0.22) |   |   | 0.30 |   |   |   |   |   |   |
|   |   | Cationized PVA *13 (0.35) |   |   |   | 0.30 |   |   |   |   |   |
|   |   | Cationized hydroxypropyl cellulose *14 (0.5) |   |   |   |   | 0.30 |   |   |   |   |
|   | Cation charge density of the whole of component (E) (meq/g) |   | 1.1 | 1.3 | 0.22 | 0.35 | 0.5 | 1.3 | 1.3 | 1.1 | 1.1 |
| (F) | Polyvinyl alcohol *15 |   |   |   |   |   |   |   | 0.30 |   |   |
| Others | Ascorbic acid |   | 0.20 | 0.20 | 0.20 | 0.20 | 0.20 | 0.20 | 0.20 | 0.20 | 0.20 |
|   | Silicone *16 |   | 5.00 | 5.00 | 5.00 |   | 5.00 |   |   | 5.00 | 5.00 |

TABLE 2-continued

|  |  |  |  |  |  |  |  |  |  |  |
|---|---|---|---|---|---|---|---|---|---|---|
|  | Ampholytic surfactant (lauric acid amide propyl betaine (28.8%)) *17 |  | 20.10 | 20.10 | 20.10 |  | 20.10 |  |  | 20.10 | 20.10 |
|  | Water |  | 11.19 | 11.19 | 11.19 | 36.10 | 11.19 | 33.39 | 33.09 | 11.39 | 10.89 |
| Total |  |  | 100.0 | 100.0 | 100.0 | 100.0 | 100.0 | 100.0 | 100.0 | 100.0 | 100.0 |
| (A)/(E) mass ratio |  |  | 0.57 | 0.57 | 0.57 | 0.57 | 0.57 | 0.57 | 0.57 | 1.71 | 0.29 |
| Evaluation | ΔE | Hair dyeing: 6 times | 14.7 | 15.7 | — | — | — | — | — | 10.5 | 13.5 |
|  |  | Hair dyeing: 15 times | 31.4 | 31.5 | 29.6 | 30.6 | 32.0 | 30.9 | 37.1 | — | — |

|  |  |  | Example |  |  |  |  |  |  | Comparative Example |  |
|---|---|---|---|---|---|---|---|---|---|---|---|
|  |  |  | 16 | 17 | 18 | 19 | 20 | 21 | 22 | 3 | 4 |
| (A) | Compound represented by the general formula (1) or its salt | (A1) 5,6-Dihydroxyindole solution *1 | 15.00 | 15.00 | 15.00 | 15.00 | 15.00 | 15.00 | 15.00 | 15.00 | 15.00 |
| (B) | Alkaline agent | Monoethanolamine | 1.50 | 1.50 | 1.50 | 1.50 | 1.50 | 1.50 | 1.50 | 1.50 | 1.50 |
| (C) | Buffering agent | Sodium bicarbonate | 2.00 | 2.00 | 2.00 | 2.00 | 2.00 | 2.00 | 2.00 | 2.00 | 2.00 |
|  |  | Phosphoric acid (75%) *2 | 0.31 | 0.31 | 0.31 | 0.31 | 0.31 | 0.31 | 0.31 | 0.31 | 0.31 |
|  |  | Citric acid |  |  |  |  |  |  |  |  |  |
| (D) | Anionic surfactant | POE lauryl ether sulfuric acid Na (27.0%) *3 | 44.40 | 44.40 | 44.40 | 44.40 | 44.40 | 44.40 | 44.40 | 44.40 | 44.40 |
|  |  | POE lauryl ether acetic acid Na (18.2%) *4 |  |  |  |  |  |  |  |  |  |
| (E) | Cationic polymer (cation charge density: meq/g) | Cationized guar gum *10 (1.1) | 1.00 | 0.19 | 0.12 | 0.090 |  |  |  |  | 0.085 |
|  |  | Cationized tara gum *11 (1.3) |  |  |  |  | 0.10 | 0.60 | 1.00 |  |  |
|  |  | Cationized PVA *12 (0.22) |  |  |  |  |  |  |  |  |  |
|  |  | Cationized PVA *13 (0.35) |  |  |  |  |  |  |  |  |  |
|  |  | Cationized hydroxypropyl cellulose *14 (0.5) |  |  |  |  |  |  |  |  |  |
|  | Cation charge density of the whole of component (E) (meq/g) |  | 1.1 | 1.1 | 1.1 | 1.1 | 1.3 | 1.3 | 1.3 | — | 1.1 |
| (F) | Polyvinyl alcohol *15 |  |  |  |  |  |  |  |  |  |  |
| Others | Ascorbic acid |  | 0.20 | 0.20 | 0.20 | 0.20 | 0.20 | 0.20 | 0.20 | 0.20 | 0.20 |
|  | Silicone *16 |  | 5.00 | 5.00 | 5.00 | 5.00 | 5.00 | 5.00 | 5.00 | 5.00 | 5.00 |
|  | Ampholytic surfactant (lauric acid amide propyl betaine (28.8%)) *17 |  | 20.10 | 20.10 | 20.10 | 20.10 | 20.10 | 20.10 | 20.10 | 20.10 | 20.10 |
|  | Water |  | 10.49 | 11.30 | 11.37 | 11.40 | 11.39 | 10.89 | 10.49 | 11.49 | 11.41 |
| Total |  |  | 100.0 | 100.0 | 100.0 | 100.0 | 100.0 | 100.0 | 100.0 | 100.0 | 100.0 |
| (A)/(E) mass ratio |  |  | 0.17 | 0.90 | 1.40 | 1.90 | 1.71 | 0.29 | 0.17 | — | 2.01 |
| Evaluation ΔE | Hair dyeing: 6 times |  | 13.1 | 13.6 | 12.9 | 10.3 | 12.3 | 15.8 | 14.9 | 6.9 | 10.0 |
|  | Hair dyeing: 15 times |  | — | — | — | — | — | — | — | 16.7 | — |

TABLE 3

|  |  |  | Example |  |  |  |
|---|---|---|---|---|---|---|
|  |  |  | 23 | 24 | 25 | 26 |
| (A) | Compound represented by the general formula (1) or its salt | (A1) 5,6-Dihydroxyindole solution *1 | 5.00 | 15.00 | 30.00 | 50.00 |
| (B) | Alkaline agent | Monoethanolamine | 1.50 | 1.50 | 1.50 | 1.50 |
| (C) | Buffering agent | Sodium bicarbonate | 2.00 | 2.00 | 2.00 | 2.00 |
|  |  | Phosphoric acid (75%) *2 | 0.31 | 0.31 | 0.31 | 0.31 |
| (D) | Anionic surfactant | POE lauryl ether sulfuric acid Na (27.0%) *8 | 44.40 | 44.40 |  |  |
|  |  | POE lauryl ether sulfuric acid Na (69.9%) *18 |  |  | 17.12 | 17.12 |
| (E) | Cationic polymer (cation charge density: meq/g) | Cationized guar gum *10 (1.1) | 0.30 | 0.30 | 0.30 | 0.30 |
|  | Cation charge density of the whole of compontent (E) (meq/g) |  | 1.1 | 1.1 | 1.1 | 1.1 |
| Others | Ascorbic acid |  | 0.20 | 0.20 | 0.20 | 0.20 |
|  | Silicone *16 |  | 5.00 | 5.00 | 5.00 | 5.00 |

TABLE 3-continued

|  |  |  | Example | | | |
|---|---|---|---|---|---|---|
|  |  |  | 23 | 24 | 25 | 26 |
|  | Ampholytic surfactant (lauric acid amide propyl betaine (28.8%)) *17 |  | 20.10 | 20.10 | 20.10 | 20.10 |
|  | Water |  | 21.19 | 11.19 | 23.47 | 3.47 |
| Total |  |  | 100.0 | 100.0 | 100.0 | 100.0 |
| (A)/(E) mass ratio |  |  | 0.19 | 0.57 | 1.14 | 1.90 |
| Evaluation ΔE |  | Hair dyeing: 3 times | 5.6 | 10.0 | 14.0 | 19.0 |
|  |  | Hair dyeing: 6 times | 10.2 | 17.1 | 22.3 | 23.8 |

TABLE 4

|  |  |  | Example | | |
|---|---|---|---|---|---|
|  |  |  | 24 | 27 | 28 |
| (A) | Compound represented by the general formula (1) or its salt | (A1) 5,6-Dihydroxyindole solution *1 | 15.00 | 15.00 | 15.00 |
| (B) | Alkaline agent | Monoethanolamine | 1.50 | 1.50 | 1.50 |
| (C) | Buffering agent | Sodium bicarbonate | 2.00 | 2.00 | 2.00 |
|  |  | Phosphoric acid (75%) *2 | 0.31 | 0.31 | 0.31 |
| (D) | Anionic surfactant | POE lauryl ether sulfuric acid Na (27.0%) *3 | 44.40 | 44.40 | 44.40 |
| (E) | Cationic polymer (cation charge density: meq/g) | Cationized guar gum *10 (1.1) | 0.30 | 0.30 | 0.30 |
|  | Cation charge density of the whole of component (E) (meq/g) |  | 1.1 | 1.1 | 1.1 |
| (F) | Polyvinyl alcohol *15 |  |  |  |  |
| Others | Ascorbic acid |  | 0.20 | 0.20 | 0.20 |
|  | Silicone *16 |  | 5.00 | 5.00 | 5.00 |
|  | Ampholytic surfactant (lauric acid amide propyl betaine (28.8%)) *17 |  | 20.10 | 20.10 | 20.10 |
|  | Oxidation dye X *19 |  |  | 0.12 |  |
|  | Oxidation dye Y *20 |  |  |  | 0.10 |
|  | Water |  | 11.19 | 11.07 | 11.19 |
| Total |  |  | 100.0 | 100.0 | 100.0 |
| (A)/(E) mass ratio |  |  | 0.57 | 0.57 | 0.57 |
| Evaluation ΔE |  | Hair dyeing: 3 times | 10.0 | 12.8 | 13.0 |
|  |  | Hair dyeing: 6 times | 17.1 | 22.2 | 21.5 |

TABLE 5

|  |  |  | Example | | |
|---|---|---|---|---|---|
|  |  |  | 29 | 30 | 31 |
| (A) | Compound represented by the general formula (1) or its salt | (A1) 5,6-Dihydroxyindole solution *1 | 15.00 |  |  |
|  |  | (A2) 5,6-Dihydroxyindole solution *2 |  | 15.00 |  |
|  |  | (A3) 5,6-Dihydroxyindoline HBr•solution *22 |  |  | 15.00 |
| (B) | Alkaline agent | Monoethanolamine | 1.50 | 1.50 | 1.50 |
| (C) | Buffering agent | Sodium bicarbonate | 2.00 | 2.00 | 2.00 |
|  |  | Phosphoric acid (75%) *2 | 0.31 | 0.31 | 0.31 |
| (D) | Anionic surfactant | POE lauryl ether sulfuric acid Na (27.0%) *3 | 44.40 | 44.40 | 44.40 |
| (E) | Cationic polymer (cation charge density: meq/g) | Cationized guar gum *10 (1.1) | 0.30 | 0.30 | 0.30 |
|  | Cation charge density of the whole of component (E) (meq/g) |  | 1.1 | 1.1 | 1.1 |
| (F) | Polyvinyl alcohol *15 |  |  |  |  |
| Others | Ascorbic acid |  | 0.20 | 0.20 | 0.20 |
|  | Silicone *16 |  | 5.00 | 5.00 | 5.00 |
|  | Ampholytic surfactant (lauric acid amide propyl betaine (28.8%)) *17 |  | 20.10 | 20.10 | 20.10 |
|  | Water |  | 11.19 | 11.19 | 11.19 |

TABLE 5-continued

|  |  | Example | | |
|---|---|---|---|---|
|  |  | 29 | 30 | 31 |
| Total |  | 100.0 | 100.0 | 100.0 |
| (A)/(E) mass ratio |  | 0.57 | 0.50 | 0.50 |
| Evaluation ΔE | Hair dyeing: 3 times | 11.9 | 14.2 | 7.3 |
|  | Hair dyeing: 6 times | 20.8 | 21.2 | 10.9 |

The components described in the tables are shown below. All of the blending amounts (% by mass) of the respective components described in the tables are tangible.

*1: (A1) 5,6-Dihydroxy indole solution; solution produced by the method described in Japanese Patent No. 5570161 (5,6-dihydroxyindole: 1% by mass, 5,6-dihydroxyindole-2-carboxylic acid: 0.14% by mass, ethanol: 20% by mass, water:remainder)

*2: Phosphoric acid; Food additive 75% phosphoric acid (manufactured by Nippon Chemical Industrial Co., Ltd.)

*3: Sodium polyoxyethylene lauryl ether sulfate; EMAL E-27C (manufactured by Kao Corporation, active component amount: 27% by mass)

*4: Sodium polyoxyethylene lauryl ether acetate; AKYPO LM-26SD (manufactured by Kao Corporation, active component amount: 18.2% by mass)

*5: Polyquaternium-7 (diallyldimethylammonium chloride/acrylamide copolymer); MERQUAT 550 (manufactured by Lubrizol Advanced Materials, cation charge density (literature value)=3.1 meq/g)

*6: Polyquaternium-10 (o-[2-hydroxy-3-(trimethylammonio)propyl]hydroxyethyl cellulose chloride); CATICELO M-80 (manufactured by Kao Corporation, cation charge density=1.0 meq/g)

*7: Polyquaternium-52 (N,N-dimethylaminoethyl methacrylate diethyl sulfate/N,N-dimethyl acrylamide/dimethacrylic acid polyethylene glycol copolymer); SOFCARE KG-101W-E (manufactured by Kao Corporation, cation charge density (literature value)=0.8 meq/g)

*8: Polyquaternium-22 (diallyldimethylammonium chloride/acrylic acid copolymer); MERQUAT 280 (manufactured by Lubrizol Advanced Materials, cation charge density=2.2 meq/g)

*9: Polyquaternium-6 (polydiallyldimethylammonium chloride); MERQUAT 100 (manufactured by Lubrizol Advanced Materials, cation charge density (literature value)=6.2 meq/g)

*10: Cationized guar gum: JAGUAR EXCEL (manufactured by Solvay (Novecare), cation charge density=1.1 meq/g)

*11: Cationized tara gum: CATINAL CTR-100 (manufactured by Toho Chemical Industry Co., Ltd., cation charge density=1.3 meq/g)

*12: Cationized polyvinyl alcohol: GOHSENX K-434 (manufactured by The Nippon Synthetic Chemical Industry Co., Ltd., cation charge density=0.22 meq/g)

*13: Cationized polyvinyl alcohol: CM318 (manufactured by Kuraray Co., Ltd., cation charge density=0.35 meq/g)

*14: Cationized hydroxypropyl cellulose: SOFCARE C-HP2 (manufactured by Kao Corporation, cation charge density=0.5 meq/g)

*15: Polyvinyl alcohol: JL-25E (manufactured by JAPAN VAM & POVAL CO., LTD., average degree of polymerization=2,500, degree of saponification=79 to 81%)

*16: Silicone: SILICONE SH 200C FLUID 10 CS (manufactured by Dow Corning Toray Co., Ltd.)

*17: Ampholytic surfactant (lauric acid amide propyl betaine): AMPHITOL 20AB (manufactured by Kao Corporation, active component amount: 28.8% by mass)

*18: Sodium polyoxyethylene lauryl ether sulfate; EMAL 270J (manufactured by Kao Corporation, active component amount: 69.9% by mass)

*19: Oxidation dye X; Toluene-2,5-diamine sulfate: 0.02% by mass, paraaminophenol: 0.02% by mass, metaaminophenol: 0.02% by mass, resorcin: 0.02% by mass, 2,4-diaminophenoxyethanol hydrochloride: 0.02% by mass, and 2-methyl-5-aminophenol: 0.02% by mass (all of the term "% by mass" mean the amount relative to the whole amount of the hair cosmetic)

*20: Oxidation dye Y Paraphenylenediamine sulfate: 0.02% by mass, 4-aminometacresol: 0.02% by mass, 2-methylresorcin: 0.02% by mass, 2-amino-3-hydroxypyridine: 0.02% by mass, and 2-amino-4-(8-hydroxyethyl)aminoanisole sulfate: 0.02% by mass, (all of the term "% by mass" mean the amount relative to the whole amount of the hair cosmetic)

*21: (A2) 5,6-Dihydroxyindole solution (manufactured by Matrix Scientific, 5,6-dihydroxyindole: 1% by mass, ethanol: 20% by mass, water:remainder)

*22: (A3) 5,6-Dihydroxyindoline hydrobromide solution (manufactured by AK-scientific, 5,6-dihydroxyindoline hydrobromide: 1% by mass, ethanol: 20% by mass, water: remainder)

The following were noted from Tables 1 to 5.

As shown in Examples 1 to 31, the hair cosmetic of the present invention reveals high hair dyeing properties.

From comparison of Examples 1 to 6 with Comparative Example 1 in Table 1, in which the same components other than the component (E) are blended, it is noted that in the case where the cation charge density of the cationic polymer as the component (E) to be used in the hair cosmetic is more than the prescribed scope of the present invention, the hair dyeing properties are lowered.

From the results in Examples 5 and 6 in Table 1, it is noted that even in the case where the cationic polymer having a cation charge density of more than 4.8 meq/g is combined and used as the component (E), the effects of the invention can be obtained so long as the cation charge density of the whole of the component (E) falls within the prescribed scope of the present invention.

From comparison of Examples 1 to 6 with Comparative Example 2 in Table 1 and comparison of Examples 7 to 11 with Comparative Example 3 in Table 2, it is noted that in the case where the hair cosmetic does not contain the cationic polymer, the hair dyeing properties are lowered. In addition, as shown in Examples 7 to 11 in Table 2, the hair dyeing properties of the hair cosmetic do not depend upon the molecular structure of the cationic polymer of the component (E) but are greatly influenced by the cation charge density.

From comparison of Examples 8 and 12 and Example 13 in Table 2, it is noted that by blending polyvinyl alcohol, the hair dyeing properties of the hair cosmetic are more improved (see Example 13).

In Table 2, Examples 14 to 19 and Examples 20 to 22 are each an example in which the blending amount of the component (E) in the hair cosmetic is changed. In accordance with comparison between Example 7 and Examples 14 to 19 and comparison between Example 8 and Examples 20 to 22, when the blending amount of the component (E) is in a range of 0.3 to 0.6% by mass, the hair dyeing properties were more favorable. In addition, in accordance with comparison of Examples 7 and 14 to 19 with Comparative Example 4, when the mass ratio (A/(E)) is in a range of 0.05 or more and less than 2, and especially 0.05 or more and 1.5 or less, the hair dyeing properties were more favorable.

In Table 3, Examples 23 to 26 are each an example in which the blending amount of the component (A) in the hair cosmetic is changed, and in accordance with comparison between Example 7 and Examples 23 to 26, as the blending amount of the component (A) was larger, the hair dyeing properties were more improved.

In Table 4, Examples 27 and 28 are each an example in which the oxidation dye was further blended in Example 24, and as compared with the case where the dye is only the component (A), the hair dyeing properties were more improved.

In addition, Examples 29 to 31 in Table 5 are an example in which the kind of the component (A) in the hair cosmetic is changed.

INDUSTRIAL APPLICABILITY

In accordance with the hair cosmetic of the present invention, even when a hair dye is not used, it is possible to simply obscure gray hairs through a daily hair care behavior, such as shampooing, and to obtain a high gray hair dyeing effect for a short period of time.

The invention claimed is:

1. A hair cosmetic, comprising:
   (A) from 0.05% by mass to 5% by mass of a compound represented by formula (1) or a salt thereof:

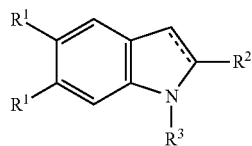

(1)

wherein a broken line represents the presence or absence of a π bond; $R^1$ represents a hydroxy group or an acetoxy group; $R^2$ represents a hydrogen atom or —COOR, where R is a hydrogen atom, a methyl group, or an ethyl group; and $R^3$ represents a hydrogen atom, an acetyl group, a methyl group, or an ethyl group;
   (B) an alkaline agent;
   (C) a buffering agent;
   (D) from 3% by mass to 40% by mass of an anionic surfactant; and
   (E) from 0.05% by mass to 5% by mass of a cationic polymer having a cation charge density of from 0.01 meq/g to 4.8 meq/g,
   wherein a mass ratio of the component (A) to the component (E) [(A)/(E)] is from 0.05 to less than 2.

2. The hair cosmetic according to claim 1, wherein the mass ratio of the component (A) to the component (E) [(A)/(E)] is from 0.05 to 1.5.

3. The hair cosmetic according to claim 1, wherein the component (B) comprises at least one selected from the group consisting of ammonia and an alkanolamine.

4. The hair cosmetic according to claim 1, wherein a pH is from 8.0 to 12.0.

5. The hair cosmetic according to claim 1, further comprising:
   (F) at least one polymer selected from the group consisting of polyvinyl alcohol and polyvinylpyrrolidone.

6. The hair cosmetic according to claim 1, which is a hair cleansing agent.

7. A method for dyeing hair, comprising:
   applying the hair cosmetic according to claim 1 on hair.

8. The hair cosmetic according to claim 1, wherein the content of the component (D) in the hair cosmetic is from 5% by mass to 30% by mass.

9. The hair cosmetic according to claim 1, wherein the component (D) comprises at least one selected from the group consisting of an alkyl ether sulfate and an alkyl ether carboxylate.

10. The hair cosmetic according to claim 1, wherein the component (C) comprises at least one basic component selected from the group consisting of sodium carbonate, potassium carbonate, sodium bicarbonate, potassium bicarbonate, glycine, sodium tetraborate, and ammonium chloride.

11. The hair cosmetic according to claim 1, wherein the component (C) comprises at least one protonating agent selected from the group consisting of hydrochloric acid, sulfuric acid, phosphoric acid, formic acid, acetic acid, and citric acid.

12. The hair cosmetic according to claim 1, wherein the component (C) comprises:
   at least one basic component selected from sodium carbonate, potassium carbonate, sodium bicarbonate, potassium bicarbonate, glycine, sodium tetraborate, and ammonium chloride; and
   at least one protonating agent selected from the group consisting of hydrochloric acid, sulfuric acid, phosphoric acid, formic acid, acetic acid, and citric acid.

13. The hair cosmetic according to claim 1, wherein the component (C) comprises sodium bicarbonate.

14. The hair cosmetic according to claim 1, wherein the component (C) comprises sodium bicarbonate and at least one selected from the group consisting of phosphoric acid and citric acid.

15. The hair cosmetic according to claim 1, wherein the content of the component (D) is from 11.97% by mass to 40% by mass.

* * * * *